United States Patent [19]

Thompson

[11] Patent Number: 5,413,118
[45] Date of Patent: May 9, 1995

[54] SURGICAL DRAPES FOR COVERING APPENDAGES

[75] Inventor: Joseph F. Thompson, Lindenhurst, Ill.

[73] Assignee: Baxter International Inc., Deerfield, Ill.

[21] Appl. No.: 570,090

[22] Filed: Aug. 20, 1990

[51] Int. Cl.⁶ .............................................. A61F 13/00
[52] U.S. Cl. ..................................... 128/853; 128/849
[58] Field of Search ............... 128/846, 849, 850, 851, 128/852, 853, 854, 855, 856

[56] References Cited

U.S. PATENT DOCUMENTS

| | | | |
|---|---|---|---|
| 1,554,692 | 9/1925 | Shane | 128/849 |
| 2,593,121 | 4/1952 | Djorup | 128/849 X |
| 3,251,360 | 5/1966 | Melges . | |
| 3,494,356 | 3/1967 | Melges . | |
| 3,693,618 | 9/1972 | Madden . | |
| 3,715,902 | 2/1973 | Shaffer et al. | 128/853 |
| 3,750,663 | 8/1973 | Collins | 128/855 |
| 3,862,632 | 1/1975 | Hinsch . | |
| 3,920,012 | 11/1975 | Patel | 128/849 |
| 3,942,523 | 3/1976 | Rudtke . | |
| 4,105,019 | 8/1978 | Haswell | 128/849 X |
| 4,308,864 | 1/1982 | Small et al. . | |
| 4,471,769 | 9/1984 | Lockhart . | |

FOREIGN PATENT DOCUMENTS 291481  11/1988  European Pat. Off. ............ 128/849

Primary Examiner—Sam Rimell
Attorney, Agent, or Firm—Robert A. Stenzel; Paul C. Flattery

[57] ABSTRACT

A drape is described which includes a three dimensional system for covering appendages of a patient. The drape includes a top sheet which forms a first, generally horizontal plane when draped over a patient. The drape further includes an apron which is attached to the top sheet and forms second and third, generally vertical planes.

18 Claims, 5 Drawing Sheets

FIG. 6
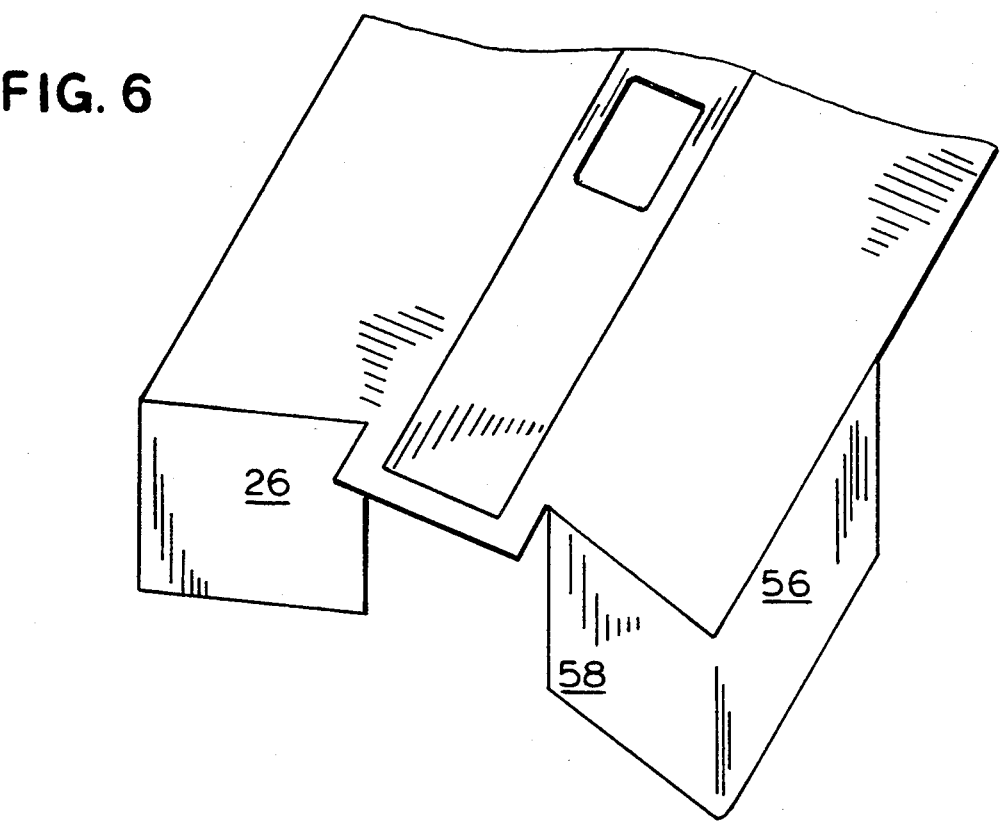
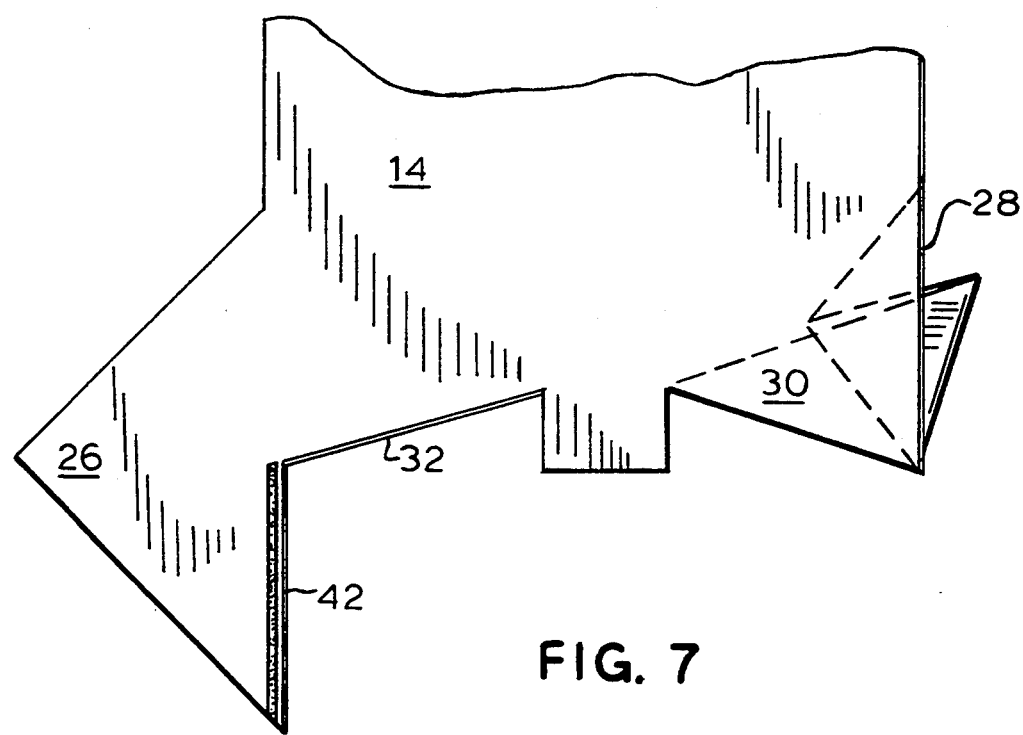
FIG. 7

SURGICAL DRAPES FOR COVERING APPENDAGES

BACKGROUND OF THE INVENTION

The invention relates generally to surgical drapes and more specifically relates to three-dimensional drapes for covering appendages of a patient.

Various techniques have been used in the past to cover the feet or other appendages of a patient during a surgical procedure. Three commonly used techniques include drapes having tubes, flaps, and envelope-type shapes. Each of these types of drapes have problems associated with them particularly when these types of drapes are used when a patient is positioned in the "low" lithotomy position and the entire patient's body needs to be covered.

For instance, surgical drapes that are in the form of tubes to cover a patient's feet and legs can be difficult to put on a patient using sterile techniques. Although tube-shaped drapes provide very good coverage over a patient's legs, the drapes are somewhat inflexible in their use. Also, since the tubes are generally separate and distinct from the drapes that are used to cover the rest of the patient, gaps may exist between the tube-shaped drapes and other drapes covering the patient. This can be highly undesirable from a sterility perspective. Another difficulty with tube-shaped drapes is that they are relatively small in size which can present problems when the entire patient needs to be draped.

Flap-type drapes are simply flat drapes which can be spread over the legs or other appendages of a patient. This type of drape can be particularly difficult to maintain in position over the curved surfaces of an appendage. Thus, flap-type drapes are generally more susceptible to sliding problems than tube-shaped drapes. In addition, when flap-type drapes are used to cover various appendages of the patient, it is typical that multiple drapes will be used. Again this presents a problem of gaps between drapes which is undesirable from a sterility perspective.

Many of the problems discussed above have been at least partially overcome through the use of envelope-shaped drapes. A sample of an envelope-shaped drape is illustrated as prior art in FIG. 1. As can be seen from the figure, an envelope-shaped drape is essentially a two-dimensional drape. When the drape is used to cover an appendage, the appendage is tucked into the inside of the envelope. However, since it is not desirable to touch or move a patient as a drape is being placed on the patient, an envelope-shaped drape can be difficult to place over a patient using sterile techniques. Generally, in order to place an envelope-shaped drape over a patient using sterile techniques, it is necessary to extend the drape past the distal end of the patient's appendage and pull the drape back toward the patient to cause the appendage to be located inside the envelope. This means that the drape needs to be substantially longer than the length of the appendage that it is intended to cover.

Therefore, a need existed to develop a new draping system for covering patients which was relatively simple to place over a patient's appendage, was formed of a single unit to eliminate gaps, and was relatively easy to maintain in position.

OBJECT OF THE INVENTION

It is the object of the invention to provide a three-dimensional draping system for covering an appendage of a patient.

It is another object of the invention to provide a single-unit that covers the torso of a patient as well as at least one appendage of a patient.

It is yet another object of the invention to provide a draping system for covering an appendage of a patient which does not require the drape to be substantially longer than the appendage to be covered.

Another object of the invention is to provide a single drape which can be used to cover substantially all of a patient in the low lithotomy position which is relatively simple and inexpensive to manufacture.

It is another object of the invention to provide a drape for covering an appendage of a patient which can be maintained in position over the patient during a surgical procedure.

These and other objects of the invention will be more apparent from the description of the invention below.

SUMMARY OF THE INVENTION

A drape is described for covering an appendage of a patient. The drape includes a top sheet having a top sheet edge. The drape further includes an upper surface and an under surface that form a first plane which is generally horizontal when the under surface of the sheet is in proximity with the appendage of the patient. The drape further includes an apron means which extends downwardly from the top sheet. At least a portion of the apron means is attached to at least a portion of the top sheet edge. The apron means forms second and third planes when the drape is positioned over the patient. The second and third planes are at an angle with respect to each other and with respect to the first plane.

BRIEF DESCRIPTION OF THE DRAWINGS

FIG. 6 illustrates an alternative embodiment of the invention in which an apron has a rectangular shape;

FIG. 7 illustrates another embodiment of the invention in which an apron means and a top sheet are formed of a single piece of material;

DETAILED DESCRIPTION OF THE PREFERRED EMBODIMENT

Figure 2:
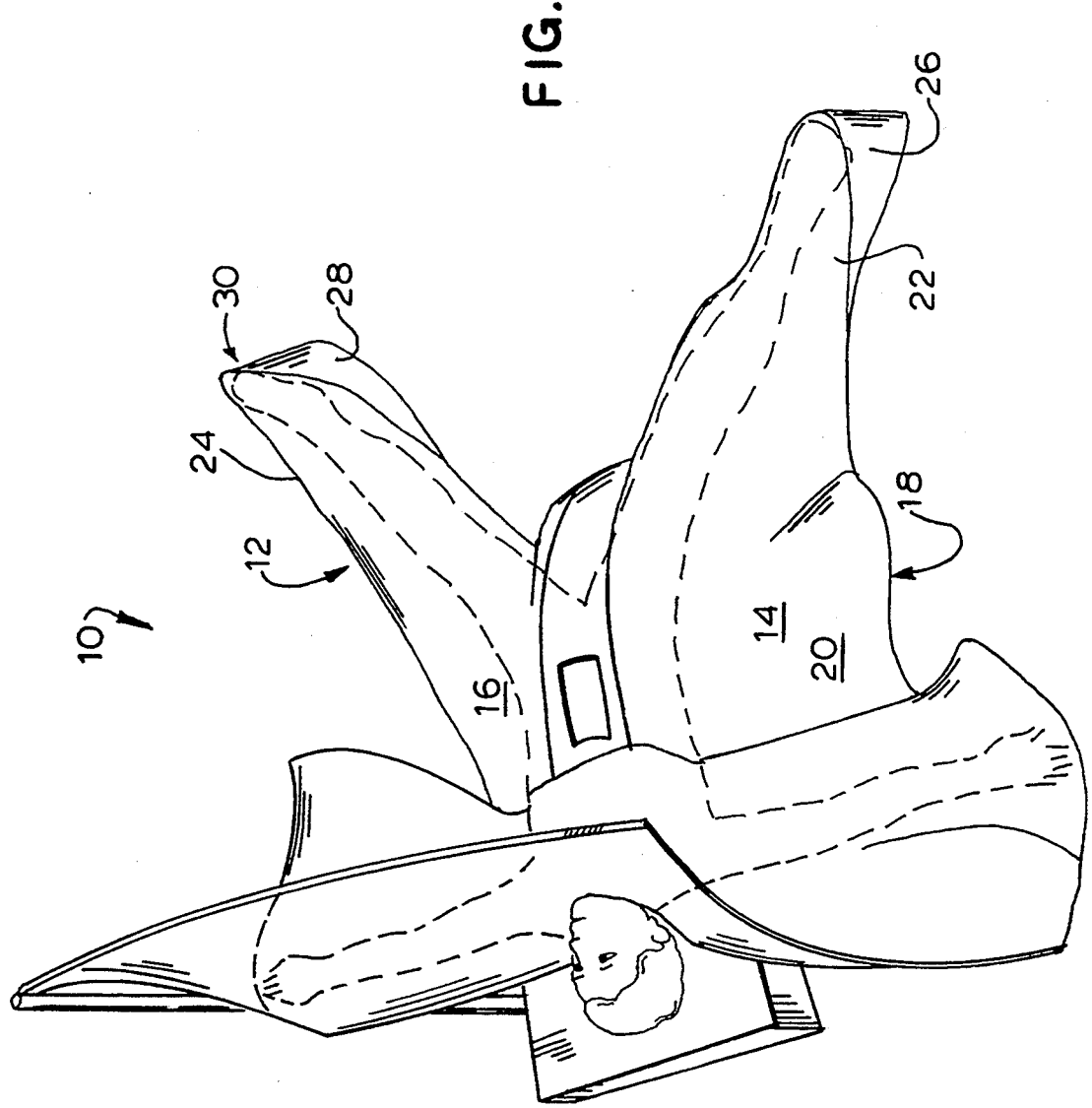
FIG. 2 is a perspective view of a currently preferred embodiment of the invention when the drape is in the open position over a patient.

Refer now to FIG. 2 which is a perspective view of the currently preferred embodiment of the invention, In this figure, a patient is positioned in the low lithotomy position, The drape 10 includes a lower section 12 for covering the feet of the patient, The drape also includes a top sheet 14 that has an upper surface 16 and an under surface 18, The surfaces of the top sheet 14 form a first plane 20 which is generally horizontal when the under surface 18 of the top sheet 14 is in proximity with the appendage of the patient.

The lower section 12 includes two halves 22, 24 which are mirror images of each other. Each half includes an apron means 26 which extends downwardly from the top sheet 14. The apron means forms second and third planes 28, 30 when the drape is positioned over the patient.

Figure 1:
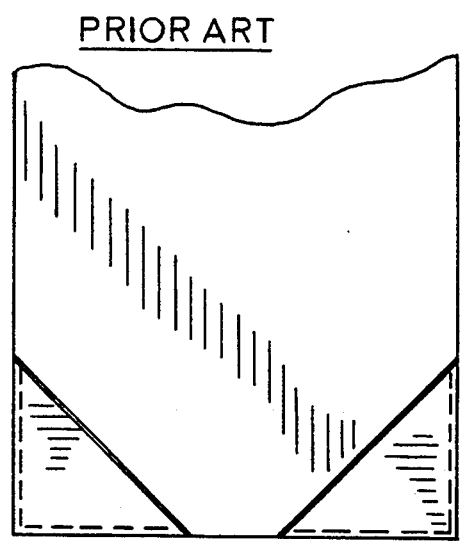
FIG. 1 illustrates a prior-art, envelope-type drape.
Figure 3:
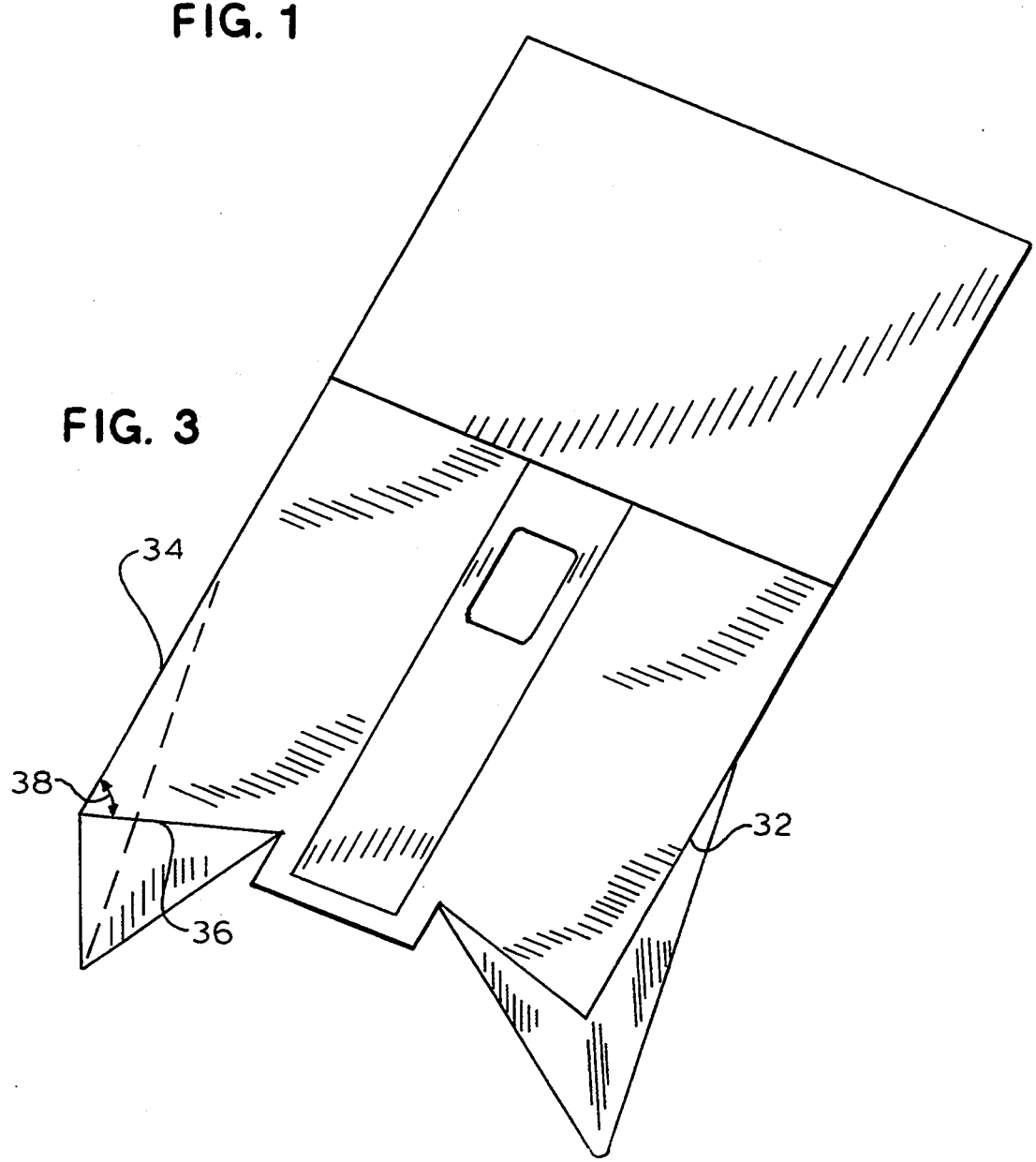
FIG. 3 is another perspective view of the preferred embodiment of the invention when the drape is in the open position.

Each side of the mirror image of the lower section 12 includes a top sheet edge 32 as illustrated in FIG. 3. In the preferred embodiment, each top sheet edge 32 includes first and second top sheet edge portions 34, 36. The first and second top sheet edge portions form an angle 38 with each other. The angle may be a right, obtuse, or acute angle. As used in this description of the invention, the word "angle" is not intended to include 180° angles. In the preferred embodiment of the invention, the first and second top sheet edge portions form an angle in the range of 70 to 75 degrees. Generally, an acute angle is preferred because it assist in maintaining the drape in position of the patient. However, in other embodiments, other angles may be used.

Figure 4:
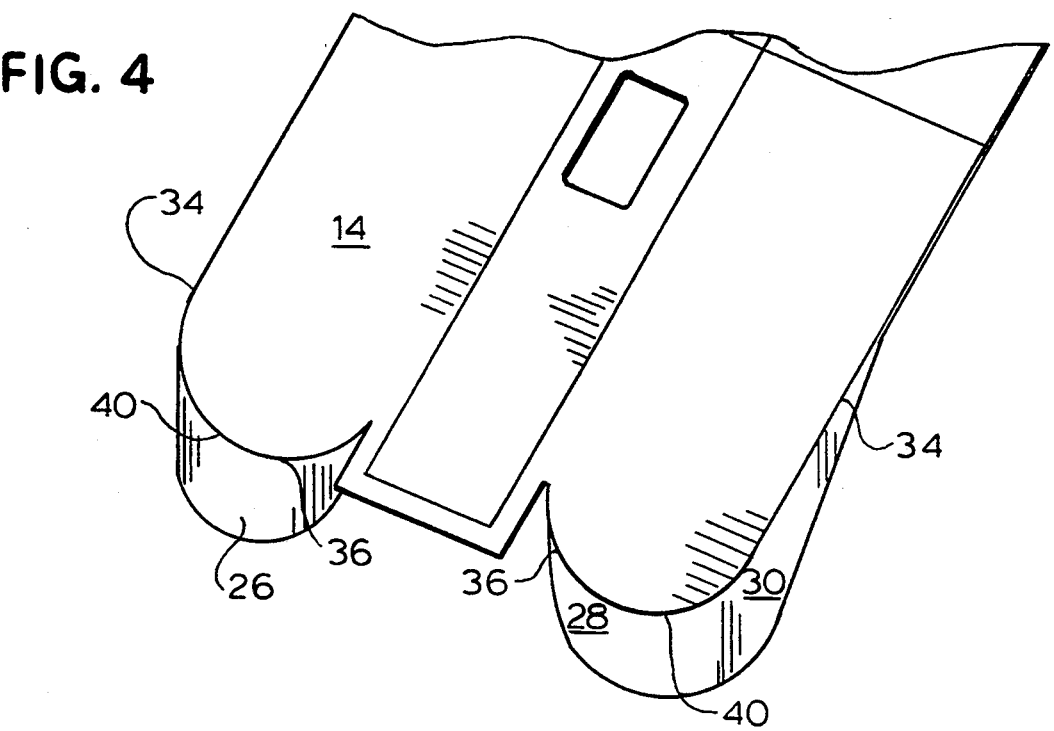
FIG. 4 illustrates another embodiment of the subject invention including an edge having a radius.

In an alternative embodiment, the two top sheet edge portions 34, 36 may be connected to one another through a third top sheet edge portion 40 that has a radius as illustrated in FIG. 4. In this embodiment, the apron means 26 extends downwardly from the top sheet 14 in a curved fashion. However, second and third planes 28, 30 are still considered to be formed by the apron means to produce a three dimensional configuration.

Figure 5:
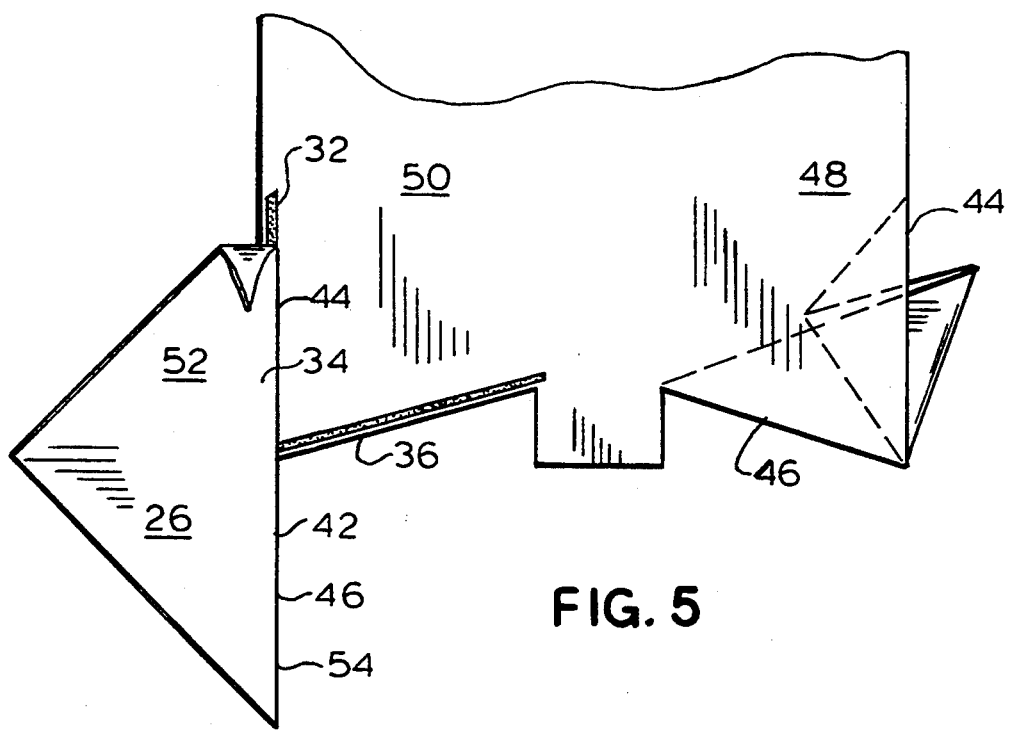
FIG. 5 illustrates a drape that has been partially manufactured.

Refer now to FIG. 5. In the preferred embodiment of the subject invention, the apron means 26 includes an apron edge 42. The apron edge 42 is attached to a portion of the top sheet edge 32. In the preferred embodiment of the invention, the apron edge 42 includes first and second apron edge portions 44, 46. The first apron edge portion 44 being connected to the first top sheet edge portion 34 and the second apron edge portion 46 being attached to the second top sheet edge portion 36. On one side 48 of the drape as illustrated in FIG. 5, the apron edge portions 44, 46 of the apron means 26 have been completely attached to the top sheet edge portions 34, 36. On the other side 50 of the drape, apron edge portion 46 have not been attached to top sheet edge portion 36 to better illustrate the shape of the apron used in the preferred embodiment of the invention. As can be seen in FIG. 5, in the preferred embodiment of the invention the apron means is formed from a single apron sheet 52 which is generally triangular in shape. In the preferred embodiment of the invention, the triangular shape of the apron sheet 52 includes a longest edge 54. The first and second apron edge portions 44, 46 are located along this longest edge 54. In one embodiment of the invention the triangular shape may be a right triangle and the apron edge 54 may be located along the longest edge of the triangle which forms the hypotenuse.

Various shapes may be used to form the apron means 26. Although in the preferred embodiment a single triangular shape is used, in other embodiments the apron means 26 may have a rectangular or semi-circular shape. A semi-circular shaped apron means 26 is illustrated in FIG. 4 and a rectangular shaped apron means 26 is illustrated in FIG. 6. In other embodiments of the invention, the apron may be formed of at least two sheets. An example of such an embodiment is also illustrated in FIG. 6. As can be seen in the figure, the apron means 26 may include a first sheet 56 which forms the second plane 28 and a second sheet 58 which forms the third plane 30.

In another embodiment of the invention, at least a portion of the apron and at least a portion of the top sheet 14 may be cut from the same piece of material. This is illustrated in FIG. 7. In the particular embodiment illustrated in this figure, the entire apron means 26 is cut from the same piece of material which forms the top sheet 14. The top sheet edge 32 is simply attached to the apron edge 42 to form the second and third planes 28, 30 of the apron means 26. Thus, the apron means and the top sheet can be formed from a single piece of material in one embodiment of the invention.

Figure 8:
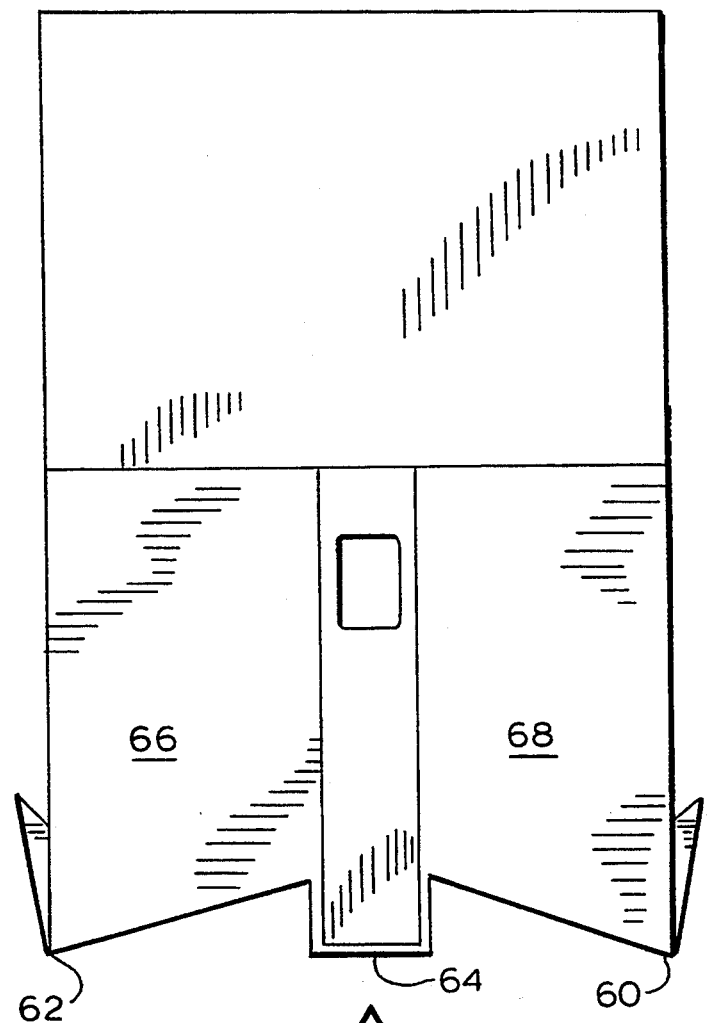
FIG. 8 illustrates a top view of the top sheet of the preferred embodiment of the subject invention.

Generally however, it is preferable to have the apron means formed from a separate piece of material to economize on the width and length of material require to form the top sheet 14. With this in mind, in the preferred embodiment of the invention, when the drape is used to cover the patient in the low lithotomy position, it is preferable that the angle portions 60, 62 of the top sheet do not extend below the flap portion 64 of the drape 10. In the preferred embodiment of the invention, the flap portion 64 is located between each of the leg portions 66, 68 of the top sheet as illustrated in FIG. 8.

The apron may be attached to the top sheet using a variety of techniques depending on the types of material used to form each section of the sheet. If the apron and the top sheet are both formed from a nonwoven fabric, the two pieces may be adhesively fastened or sewn together. If the pieces of the drape are formed from certain types of spun-bonded material, the pieces may be heat or ultrasonically sealed together.

Although the invention has been described in detail specifically for use in covering a patient's legs and feet while the patient is in the low lithotomy position, similar drapes can easily be formed to cover a patient's arms or head.

Figure 9A:
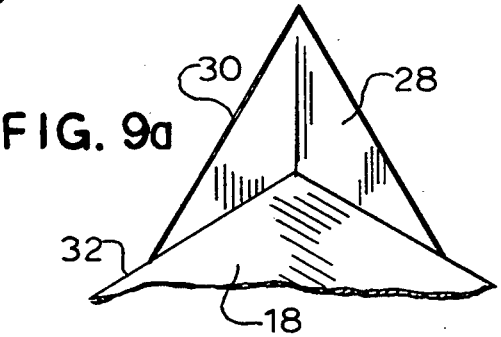
FIGS. 9(a) (b) and (c) illustrates a drape as it is being folded.
Figure 9C:
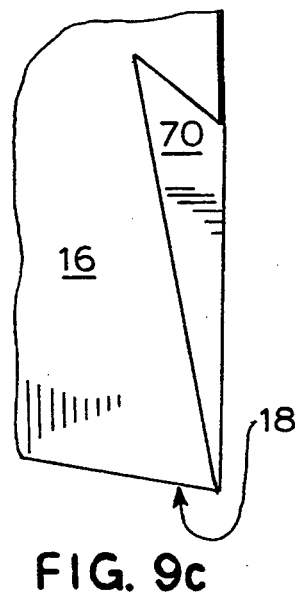
Figure 9B:
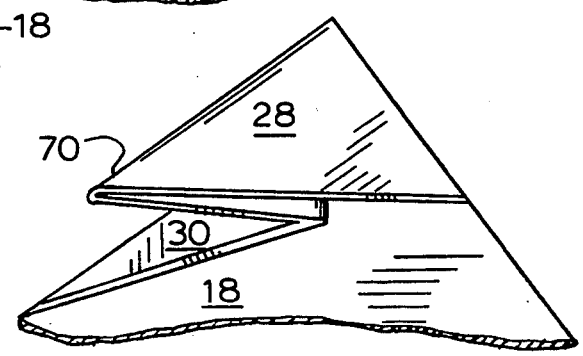

One feature of the preferred embodiment of the invention is that the apron means 26 can be folded in such a manner as to cause a flap to be formed on the upper surface of the top sheet. The flap can be used by medical personnel when unfolding the apron means and extending the apron means beyond the distal end of an appendage of a patient. More specifically, referring now to FIGS. 9(a) and (b), the portions of the apron which form the second and third planes 28, 30 are folded against the under surface 18 of the top sheet to cause the apron to lie flat against the under surface and to form a flap 70 that extends beyond the top sheet edge 32. The flap 70 can then be folded over the upper surface 16 of the top sheet as illustrated in FIG. 9(c). The flap 70 normally lays flat against the upper surface 16 until medical personnel grasp the flap 70 to unfold the apron means 26 and to extend the apron means over and beyond an appendage of a patient during positioning the top sheet 14 over a patient.

Thus, one aspect of the invention is a method for folding a drape having a top sheet in which the top sheet has upper and lower surfaces and the drape has an apron which extends downwardly from the top sheet. The method includes the steps of folding the apron against the under surface of the top sheet to cause the apron to lay flat against the under surface and to extend beyond an edge of the top sheet to form a flap. The method includes the subsequent steps of folding the flap about the edge of the top sheet to cause the flap to lay flat upon the upper surface of the top sheet. A flap thus formed allows medical personnel to grasp the flap from the upper surface when unfolding and extending the apron beyond an appendage of a patient during placement of the drape on the patient.

We claim:

1. A drape for covering an appendage of a patient, comprising: a top sheet having a top sheet edge, an upper surface and an under surface, said surfaces of said sheet forming a first plane which is generally horizontal when said under surface of said sheet is in proximity with the appendage of the patient; and apron means extending vertically downwardly from said top sheet and attached to at least a portion of said top sheet edge, said apron means forming second and third planes when said drape is positioned over the patient, said second and third planes being generally perpendicular to said first plane.

2. A drape as recited in claim 1 wherein said top sheet edge includes first and second top sheet edge portions, said first and second top sheet edge portions form an angle with one another.

3. A drape as recited in claim 2 wherein said first and second top sheet edge portions form a generally perpendicular angle.

4. A drape as recited in claim 2 wherein said first and second top sheet edge portions form an acute angle.

5. A drape as recited in claim 2 wherein said first and second top sheet edge portions form an obtuse angle.

6. A drape as recited in claim 2 wherein said first and second top sheet edge portions are connected to one another by a third top sheet edge portion, said third top sheet edge portion having a radius.

7. A drape as recited in claim 1 wherein said apron means further includes an apron edge, said apron edge being attached to said top sheet edge.

8. A drape as recited in claim 7 wherein:

said apron edge further includes first and second apron edge portions;

said top sheet edge further includes first and second top sheet edge portions which form an angle; and said first apron edge portion being connected to said first top sheet edge portion and said second apron edge portion being connected to said second top sheet edge portion.

9. A drape as recited in claim 1 wherein said apron means is formed of a single apron sheet.

10. A drape as recited in claim 9 wherein said apron sheet has a generally triangular shape.

11. A drape as recited in claim 8 wherein said apron means is formed of a single apron sheet and has a generally triangular shape.

12. A drape as recited in claim 11 wherein said triangular shape of said apron sheet includes a longest edge and said apron edge is located on said longest edge.

13. A drape as recited in claim 12 wherein said triangular shape forms a right triangle and said apron edge is located along said longest edge Forming the hypotenuse.

14. A drape as recited in claim 9 wherein said apron sheet has at least three edges.

15. A drape as recited in claim 9 wherein said apron sheet has a generally semicircular shape.

16. A drape as recited in claim 9 wherein said apron sheet has a generally rectangular shape.

17. A drape as recited in claim 1 wherein said apron means is formed of at least two sheets, one sheet forming said second plane and another sheet forming said third plane.

18. A drape for covering the feet of a patient, comprising: a top sheet having an upper and under surfaces, said surfaces of said sheet forming a first plane which is generally horizontal when said under surface of said sheet is in proximity with the feet of the patient, said top sheet having two halves which are mirror images of one another, each half having first and second top sheet edge portions; and first and second aprons for each foot, said first and second aprons being mirror images of one another, each of said aprons including first and second apron edge portions for attachment to said first and second top edge portions, respectively, each of said aprons extending vertically downwardly from said top sheet edge portions to form second and third planes when said drape is positioned over the feet of the patient, said second and third planes being generally perpendicular to said first plane.

* * * * *